US010729626B2

(12) United States Patent
Potnis et al.

(10) Patent No.: US 10,729,626 B2
(45) Date of Patent: Aug. 4, 2020

(54) STORAGE-STABLE SOLID PEROXYMONOSULFATE COMPOSITION

(71) Applicant: COLGATE-PALMOLIVE COMPANY, New York, NY (US)

(72) Inventors: Shashank Vishwanath Potnis, Thane (IN); Rolando B. Plata, Mumbai Powai (IN); Manisha Jha, Mumbain Maharashtra State (IN); Devendra Chavan, Mumbai Maharashtra State (IN)

(73) Assignee: Colgate-Palmolive Company, New York, NY (US)

( * ) Notice: Subject to any disclaimer, the term of this patent is extended or adjusted under 35 U.S.C. 154(b) by 123 days.

(21) Appl. No.: 15/385,148

(22) Filed: Dec. 20, 2016

(65) Prior Publication Data
US 2017/0181942 A1 Jun. 29, 2017

(30) Foreign Application Priority Data

Dec. 23, 2015 (IN) ............................ 4261/DEL/2015

(51) Int. Cl.
*A61K 8/23* (2006.01)
*A61Q 11/00* (2006.01)
*A61K 8/24* (2006.01)
*A61K 8/02* (2006.01)
*A61K 8/26* (2006.01)
*A61K 8/19* (2006.01)

(52) U.S. Cl.
CPC .............. *A61K 8/23* (2013.01); *A61K 8/022* (2013.01); *A61K 8/0216* (2013.01); *A61K 8/0225* (2013.01); *A61K 8/0245* (2013.01); *A61K 8/19* (2013.01); *A61K 8/24* (2013.01); *A61K 8/26* (2013.01); *A61Q 11/00* (2013.01); *A61K 2800/31* (2013.01); *A61K 2800/92* (2013.01)

(58) Field of Classification Search
CPC ... A61K 8/19; A61K 8/23; A61K 8/24; A61K 8/26; A61K 8/0216; A61K 8/022; A61K 8/0225; A61K 8/0245; A61K 2800/31; A61K 2800/92; A61Q 11/00
See application file for complete search history.

(56) References Cited

U.S. PATENT DOCUMENTS

| 3,337,466 | A | * | 8/1967 | Puetzer | A61K 8/20 252/186.31 |
| 3,556,711 | A | * | 1/1971 | Stalter | A61K 8/23 252/186.38 |
| 3,666,399 | A | * | 5/1972 | Castrantas | A61K 8/24 8/111 |
| 4,024,636 | A | * | 5/1977 | Colpitts | A61C 13/04 433/199.1 |
| 4,062,793 | A | | 12/1977 | Schodel | |
| 4,273,759 | A | | 6/1981 | Gaffar et al. | |
| 4,292,211 | A | * | 9/1981 | Herman | C11D 3/50 510/407 |
| 4,309,410 | A | | 1/1982 | Gaffar | |
| 5,032,178 | A | | 7/1991 | Cornell | |
| 5,240,697 | A | * | 8/1993 | Norfleet | A61K 8/19 424/49 |
| 5,736,158 | A | * | 4/1998 | Quast | A61K 8/21 424/464 |
| 6,274,122 | B1 | * | 8/2001 | McLaughlin | A61C 19/063 128/860 |
| 2012/0029135 | A1 | | 5/2012 | Yang et al. | |

FOREIGN PATENT DOCUMENTS

| EP | 0248936 | 12/1987 |
| GB | 1374105 | 11/1974 |
| JP | 2007-112761 A | 5/2007 |
| WO | WO 1996/019193 | 6/1996 |
| WO | WO 2000/009079 | 2/2000 |
| WO | WO 2000/016737 | 3/2000 |

OTHER PUBLICATIONS

Rivas, J. et al., "Catalytic Decomposition of Potassium Monopersulfate. Influence of Variables." *Int. Scholarly Sci. Res. & Innovation* 3(9): 476-80 (2009).
International Search Report and Written Opinion of the International Searching Authority in International Application No. PCT/US2016/067784, dated Mar. 10, 2017.

* cited by examiner

*Primary Examiner* — Ali Soroush

(57) ABSTRACT

A storage-stable solid composition comprising a tooth whitening effective amount of a particulated inorganic salt of peroxymonosulfate, and a particulated drying agent.

14 Claims, No Drawings

STORAGE-STABLE SOLID PEROXYMONOSULFATE COMPOSITION

BACKGROUND

Products that are presently available to whiten teeth include a variety of different ingredients, and the primary active ingredient is often a peroxide source such as hydrogen peroxide. The use of peroxide agents can present difficulties in both formulation and long term stability of the resulting compositions. Thus, alternative oxidizing agents with improved stability are desired.

Peroxysulfuric acid, and its salts, the peroxysulfates, are powerful oxidizing and stain removing agents. They are currently used for a variety of industrial and consumer purposes, including denture cleaning. The most common peroxymonosulfate oxidizing agent is potassium peroxymonosulfate, commonly referred to as MPS.

Potassium monoperoxysulfate has seen limited use in dental whitening compositions because of its instability in aqueous solution, especially in aqueous solution near or above neutral pH. In fact, potassium monoperoxysulfate has been known to degrade even in the presence of small quantities of water and heat. Thus, there is a need to provide a stabilized oral care product containing an effective amount of potassium monoperoxysulfate. It is desirable to provide improved oral care formulations which combine the relative stability of monoperoxysulfate salts in an anhydrous environment, with effective whitening and dispensing characteristics.

BRIEF SUMMARY

The invention concerns a solid composition, e.g., a tablet or powder, containing an oxidizing agent comprising inorganic salts of peroxymonosulfate, preferably alkaline metal salts and alkaline earth metal salts or mixtures thereof. The compositions disclosed herein include drying agents to provide enhanced shelf-life. In some embodiments, the compositions may be added to water or an aqueous solution to be then used by a consumer as a whitening mouthrinse or paste. Once dissolved, the consumer would use the resulting liquid as a typical mouthrinse or toothpaste.

Thus, the present disclosure concerns a storage-stable solid composition comprising: a tooth whitening effective amount of a particulated inorganic salt of peroxymonosulfate; and a particulated drying agent.

Further areas of applicability of the present disclosure will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Open terms such as "include," "including," "contain," "containing" and the like mean "comprising." In this description, unless otherwise stated, the use of the singular also includes the plural. For example, "a lubricant" also comprehends the case where more than one lubricant is used The solid composition of the present disclosure comprises a tooth-whitening effective amount of an inorganic salt, such as a metal salt, of peroxymonosulfate. Such salts are preferably alkali metal salts and alkaline earth metal salts or mixtures thereof. Specific examples of such salts are sodium peroxymonosulfate, potassium peroxymonosulfate, ammonium peroxymonosulfate, and the like. The solid compositions of the present disclosure are commonly referred to as toothpowders.

In one embodiment, the peroxymonosulfate is potassium peroxymonosulfate (also known as MPS, potassium monopersulfate). The potassium peroxymonosulfate (an example of which is Oxone®, an oxidizing agent) may be combined to form or exist as a triple salt of potassium peroxymonosulfate, potassium hydrogen sulfate and potassium sulfate ($2KHSO_5 \cdot KHSO_4 \cdot K_2SO_4$).

Potassium peroxymonosulfate has limited stability in aqueous solutions and can be stabilized by other common toothpaste ingredients. Therefore, contact with water during processing and storage should be avoided or minimized. The solid form of the invention overcomes the stability concerns of the oxidizing agent as long as the tablet is packaged in a moisture free environment. Preferably, the solid composition, e.g., tablet, granules or powder, is individually packaged and sealed into unit dose packages (e.g., sachets).

The solid composition is typically stored in an air tight, moisture-proof package, e.g., sachets, sealed metal foil pouches, blister packs, and desiccant capped tubes. Useful packaging materials include polymeric packaging (e.g., polyethylene and polypropylene), metal foil packaging (e.g., aluminum), and combinations thereof.

The solid compositions of the present disclosure contain no water or have a low water content. As used herein, the term "low water content" means the total concentration of water, including any free water and all water contained in any ingredients. In various embodiments of the composition, the amount of water is in an amount of less than 4% by weight, or less than 3% by weight, or less than 2% by weight, or less than 1% by weight, or less than 0.5% by weight, or less than 0.1%, or about 0.0001% to about 4% by weight, or about 0.0001% to about 0.5% by weight or about 0.0001% to about 0.1% by weight.

The solid composition of the present disclosure can be in a variety of forms including, e.g., powder (e.g., a free flowing granulation), tablet, caplet (type of tablet), granule, pellet, wafer, film and bead.

The amount of peroxymonosulfate salt, e.g., potassium peroxymonosulfate, in the solid compositions of the invention is effective to result in improved tooth whitening when used twice daily in a mouthrinse or toothpaste for about three months as compared to a control mouthrinse or toothpaste without the peroxymonosulfate salt. The amount of peroxymonosulfate salt typically is about 0.5% to about 50%, in one embodiment about 0.75% to about 40%, in another embodiment about 0.75% to about 37%, in another embodiment about 7.5% to about 15%, by weight of the total composition.

The compositions of the present disclosure include one or more drying agents, for example, a hygroscopic material. Examples of drying agents include, but are not limited to, phosphates, pyrophosphates and other polyphosphates, calcium lactate, calcium lactophosphate, double salts of calcium lactate and mixtures thereof. Other drying agents include silica gels and precipitates (e.g., non-abrasive silicas); aluminas; and mixtures thereof. Specific examples include, but are not limited to, dicalcium orthophosphate dihydrate, calcium pyrophosphate, tricalcium phosphate, calcium polymetaphosphate, insoluble sodium polymetaphosphate, potassium metaphosphate, tricalcium phosphate, trimagnesium phosphate, and magnesium orthophosphate, hydrated alumina, aluminum silicate, zirconium silicates, bentonite, beta calcium pyrophosphate, or calcium carbonate. Pyrophosphate salts may also be used in the present invention as anticalculus agents or as buffering agents. Pyrophosphate salts suitable for the present compositions include dialkali metal pyrophosphate salts, tetra alkali metal pyrophosphate salts, and mixtures thereof. Disodium dihydrogen pyrophosphate, tetrasodium pyrophosphate, and tetrapotassium pyrophosphate in their unhydrated as well as hydrated forms are the preferred species. In various embodiments, the drying agents are about 0.1% to about 60%, about 1% to about 30%, about 1% to about 10%, or about 1% to about 5% by weight of the total composition, or about 2%, about 3%, about 4% or about 5%.

In some embodiments, the compositions of the present disclosure contain a buffering agent. Examples of buffering agents include anhydrous carbonates such as sodium carbonate, sesquicarbonates, bicarbonates such as sodium bicarbonate, silicates, bisulfates, phosphates such as monopotassium phosphate and dipotassium phosphate, citrates, pyrophosphates (sodium and potassium salts) and combinations thereof. The amount of buffering agent is sufficient to provide a pH of about 5 to about 9, preferable about 6 to about 8, and more preferable about 7, when the composition is dissolved in water, a mouthrinse base, or a toothpaste base. Typical amounts of buffering agent are about 5% to about 35%, in one embodiment about 10% to about 30%, in another embodiment about 15% to about 25%, by weight of the total composition.

In some embodiments, the solid compositions of the invention contain a disintegrating agent. Disintegrating agents include natural starches, such as maize starch, potato starch etc., directly compressible starches such as starch 1500, modified starches such as carboxymethyl starches and sodium starch glycolate which are available as PRIMOJEL® and EXPLOTAB® and EXPLOSOL® and starch derivatives such as amylose. Other examples are cross-linked polyvinylpyrrolidones, e.g. crospovidones available as e.g. POLYPLASDONE XL® and KOLLIDON XL®; modified celluloses such as cross-linked sodium carboxymethylcelluloses available as, e.g., AC-DI-SOL®, PRIMELLOSE®, PHARMACEL XL®, EXPLOCEL®, and NYMCEL ZSX®; alginic acid and sodium alginate; microcrystalline cellulose, e.g. AVICEL®, PHARMACEL®, EMCOCELL®, VIVAPUR®; and methacrylic acid-divinylbenzene copolymer salts available as e.g., AMBERLITE® IRP-88. Other examples of the disintegrating agent are light silicic anhydride, calcium silicate, magnesium metasilicate aluminate, and carboxymethyl cellulose. In the present invention, each of them may be used solely or two or more thereof may be used jointly. Typical amounts of disintegrating agent are about 0.5% to about 20%, in one embodiment about 1% to about 5%, in another embodiment about 1% to about 3%, by weight of the total composition.

The compositions of the present disclosure optionally contain a binder, preferably a polymeric binder, which is compatible with an oxidizing agent, which adds bulk to the compositions and assists in holding the components of the composition together when in the form of a tablet. Examples of suitable polymeric binders include, e.g., starches, natural gums, (e.g., xanthan gum), cellulose gums, microcrystalline cellulose, maltodextrins, methylcellulose, cellulose ethers, sodium carboxymethylcellulose, ethylcellulose, gelatin, polyethylene glycol, polyvinylpyrrolidone, pectins, alginates, polyacrylamides, polyvinyloxozolidone, polyvinyl alcohols and mixtures thereof. The binder can also comprise one or more non-polymeric binders such as dextrose, lactose, sucrose, sorbitol, mannitol, xylitol and the like. Typically, the binder is present in the composition in an amount of about 10% by weight to about 60% by weight, about 15% by weight to about 50% by weight, or about 25% by weight to about 40% by weight.

The solid composition of the present disclosure is optionally an effervescent composition. The term "effervescent composition" as used herein means a composition that evolves gas bubbles when contacted with water or an aqueous solution. When the solid composition of the invention is an effervescent composition, it comprises an effervescent agent. The effervescent agent preferably is an effervescent couple that includes an acid and a base. The effervescent couple is activated when contacted with water, e.g., when the composition, e.g., powder, granule, or tablet, is placed in a glass of water. The water liberates the acid and base and enables the acid and base to react with each other to produce carbon dioxide gas, which imparts carbonation to the aqueous composition.

Examples of useful acids for an effervescent composition include citric acid, ascorbic acid, malic acid, adipic acid, tartaric acid, fumaric, succinic acid, sodium acid pyrophosphate, lactic acid, hexamic acid, and acid salts and acid anhydrides thereof, and mixtures thereof. Examples of useful acid anhydrides include citraconic anhydride, glucono-D-lactone, and succinic anhydride. Examples of useful acid salts include potassium bitartrate, acid citrate salts, sodium dihydrogen phosphate, disodium dihydrogen phosphate, sodium acid sulfite, and combinations thereof. When effervescent, the acid is present in the composition in an amount of about 10% by weight to about 60% by weight, about 15% by weight to about 50% by weight, or about 25% by weight to about 40% by weight.

The base for an effervescent composition preferably is capable of generating carbon dioxide. Examples of suitable carbonate bases include sodium bicarbonate, sodium carbonate, sodium sesquicarbonate, potassium carbonate, potassium bicarbonate, calcium carbonate, magnesium carbonate, magnesium oxide, sodium glycine carbonate, L-lysine carbonate, arginine carbonate, zinc carbonate, zinc oxide and mixtures thereof. When effervescent, the base is present in the composition in an amount of about 10% by weight to about 60% by weight, about 15% by weight to about 50% by weight, or about 25% by weight to about 40% by weight.

The compositions of the present disclosure optionally contain a lubricant. Various lubricants are suitable for use in the composition including water dispersible, water soluble, water insoluble lubricants and combinations thereof. Examples of useful water soluble lubricants include sodium benzoate, polyethylene glycol, L-leucine, adipic acid, and combinations thereof. The composition can also include water insoluble lubricants including, e.g., stearates (e.g., magnesium stearate, calcium stearate and zinc stearate), oils (e.g., mineral oil, hydrogenated and partially hydrogenated vegetable oils, and cotton seed oil) and combinations thereof. Other water insoluble lubricants include, e.g., animal fats, polyoxyethylene monostearate, talc, and combinations thereof. When the composition is in the form of a tablet, the composition preferably includes a sufficient amount of lubricant to enable the composition to be formed into tablets and released from a high speed tableting press in the form of a tablet. Typically, the amount of lubricant in the composition is about 1% by weight to about 15% by weight, about 1% by weight to about 12% by weight, about 2% by weight to about 10% by weight, or about 3% by weight to about 8% by weight. In one embodiment the composition includes sodium benzoate in an amount of about 1% by weight to about 3% by weight and polyethylene glycol in an amount of about 1% by weight to about 5.5% by weight.

The solid composition of the present disclosure can optionally contain whitening agents in addition to the peroxymonosulfate salt. Whitening agents are generally materials which are effective to provide whitening of a tooth surface to which it is applied, and include agents such as hydrogen peroxide and urea peroxide. In various embodiments, the compositions of the present disclosure may optionally comprise a peroxide whitening agent, comprising a peroxide compound. A peroxide compound is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof. In some embodiments, the peroxide compound comprises hydrogen peroxide. In some embodiments, the peroxide compound consists essentially of hydrogen peroxide. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite. One or more additional whitening agents are optionally present in a tooth-whitening effective total amount. In some embodiments the compositions additionally comprise an activator, e.g., tetraacetylethylenediamine.

The solid composition optionally can also include other ingredients, e.g., flavor agents; fillers; surfactants; preservatives, e.g., sodium benzoate and potassium sorbate; color agents including, e.g., dyes and pigments; and sweeteners.

Examples of the surfactant that can be used are sodium lauryl sulfate, sorbitan fatty acid ester, polyoxyethylene (20) sorbitan monooleate (Polysorbate 80 or Tween 80), polyethylene glycol fatty acid ester, polyoxyethylene sorbitan fatty acid ester, polyoxyethylene alkyl ether, polyoxyethylene polyoxypropylene alkyl ether, polyoxyethylene polyoxypropylene block copolymer, polyoxyethylene alkyl phenyl ether, polyoxyethylene castor oil, polyoxyethylene hydrogenated castor oil, polyoxyethylene sorbitol fatty acid ester and polyoxyethylene glycerol fatty acid ester. In the present invention, each of them may be used solely or two or more thereof may be used jointly. Typical amounts of surfactant are about 0.5% to about 3%, in one embodiment about 0.75% to about 2%, in another embodiment about 1% to about 1.5%, by weight of the total composition.

Examples of the filler are crystalline cellulose, ethylcellulose, dextrin, various kinds of cyclodextrin (α-cyclodextrin, β-cyclodextrin and γ-cyclodextrin), sodium sulfate, as well as derivatives thereof and pullulan.

Useful flavor agents include natural and synthetic flavoring sources including, e.g., volatile oils, synthetic flavor oils, flavoring aromatics, oils, liquids, oleoresins and extracts derived from plants, leaves, flowers, fruits, stems and combinations thereof. Suitable flavor agents include, e.g., citric oils, e.g., lemon, orange, grape, lime and grapefruit, fruit essences including, e.g., apple, pear, peach, grape, strawberry, raspberry, cherry, plum, pineapple, apricot, and other fruit flavors. Other useful flavor agents include, e.g., aldehydes and esters (e.g., benzaldehyde (cherry, almond)), citral, i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), 2-dodedenal (citrus, mandarin) and mixtures thereof.

Suitable coloring agents include, e.g., food, drug and cosmetic (FD&C) colors including, e.g., dyes, lakes, and certain natural and derived colorants. Useful lakes include dyes absorbed on aluminum hydroxide and other suitable carriers.

Suitable sweetening agents include stevia, sugars such as sucrose, glucose, invert sugar, fructose, ribose, tagalose, sucralose, malitol, erythritol, xylitol, and mixtures thereof, saccharin and its various salts (e.g., sodium and calcium salt of saccharin), cyclamic acid and its various salts, dipeptide sweeteners (e.g., aspartame), acesulfame potassium, dihydrochalcone, glycyrrhizin, and sugar alcohols including, e.g., sorbitol, sorbitol syrup, mannitol and xylitol, and combinations thereof.

It is understood that while general attributes of each of the above categories of materials may differ, there may be some common attributes and any given material may serve multiple purposes within two or more of such categories of materials. All of the ingredients in the compositions may have functions in addition to their primary function, and may contribute to the overall properties of the composition, including its stability, efficacy, consistency, mouthfeel, taste, odor and so forth. For example, a binder may also function as a disintegrating agent and vice versa.

The solid compositions of the present disclosure can be made via techniques known in the art. Documents which disclose techniques which may be used to prepare the solid compositions of the present disclosure are U.S. Pat. Nos. 4,886,669; 6,106,861; 6,596,311; 6,743,443; 6,811,793; 7,501,409; 7,815,897; 8,377,995; and US patent application 2005/0169986, all of which are incorporated herein by reference in their entireties. In general, the ingredients and optional components can be kneaded with an organic solvent, filled in a mold and subjected to a compression-molding. The organic solvent can be an alcohol such as methanol, ethanol, propanol, isopropanol, and the like. The kneading and granulating operations carried out by adding such auxiliary agents for making the preparation and by adding such a solvent may be conducted using the conventionally used apparatus. For example, a fluidized bed granulator, a tumbling granulator, an extrusion granulator or a spray-drying drier may be used. The solid compositions may also be prepared via freeze drying.

Powders can be prepared by compounding the ingredients and optionally calcium carbonate, and, if necessary, further orally acceptable additive(s), and mixing in a conventional manner.

The powdered compositions of the present disclosure may be made by including pulverizing (and, optionally, screen filtering) particulate material to have independent particle sizes from about 0.1 to about 1 mm, about 1 to about 500 microns, about 1 to about 250 microns, about 1 to about 150 microns, about 5 to about 100 microns, about 6 to about 35 microns, about 6 to about 13 microns in average diameter of individual particles. In one embodiment, the orally acceptable particulate is pulverized so that, in a bed having a volume of at least 125 cubic millimeters, at least 99 percent of individual particles in the bed have an independent calcium carbonate particle size from about 1 to about 150 microns.

Granules can be prepared by any one of known methods for preparing granules such as dry granulation, layering granulation, impregnated-granulation, etc.

For dry granulation, a mixture of ingredients with optional additive(s) is subjected to granulation with a roller compactor, a roll granulator, etc.

For layering granulation, a mixture similar to the above is added to a rolling inactive carriers while spraying a binder solution with a centrifugal fluidized bed granulator or the like to make the mixture adhere to the carries. Examples of the inactive carrier that used in this method include crystals of sugars or inorganic salts such as crystalline lactose, crystalline cellulose, crystalline sodium chloride, etc., and spherical granules such as spherical granules of crystalline cellulose (brand name: Avicel SP, Asahi Kasei Corporation), spherical granules of crystalline cellulose and lactose (brand name: Nonpareil-NP-5 and NP-7, Freund Co., Ltd.), spherical granules of purified white sugar (brand name: Nonpareil-103, Freund Co., Ltd.), spherical granules of lactose and α starch, etc.

For impregnating granulation, a solution containing potassium peroxymonosulfate and other ingredients at an appropriate concentration is mixed with porous carriers thereby a sufficient amount of solution is made to retain in the cavities of the carrier, which is followed by drying to remove the solvent. Examples of the porous carrier that can be used include magnesium aluminometasilicate (brand name: Neusiline, Fuji Chemical Industry Co., Ltd.), calcium silicate (Florite, Eisai Co., Ltd.), etc. Examples of the solvent include ethanol, methanol, or the like.

In some embodiments, the present disclosure also concerns a method for whitening teeth comprising mixing the solid composition described herein into water, a mouthrinse base, or a toothpaste base until the composition dissolves, followed by applying the composition to the teeth.

The term "mouthwash" or "mouthrinse" generally denotes liquid formulations which are used to rinse the surfaces of the oral cavity and provide the user with a sensation of oral cleanliness and refreshment. The mouthrinse is an oral composition that is not intentionally swallowed for purposes of systemic administration of therapeutic agents, but is applied to the oral cavity, used to treat the oral cavity and then expectorated. A mouthrinse composition will usually contain an aqueous continuous phase.

A typical mouthrinse composition consists of a liquid carrier such as water, a humectant, such as glycerin, sorbitol, propylene glycol a surfactant, such as a Pluronics, sodium lauryl sulfate, a sweetening agent, such as sodium saccharin, xylitol a flavoring agent, a coloring agent, and a preservative agent, such as potassium sorbate, sodium benzoate. The composition may also include buffering agents that have the capability to buffer to a final pH of 6.5-8, such as sodium phosphates, an anti-cavity agent, such as sodium fluoride, and an anti-bacterial agent such as cetyl pyridinium chloride.

Provided is a storage-stable solid composition (Composition 1) comprising a tooth whitening effective amount of a particulated inorganic salt of peroxymonosulfate, and a particulated drying agent.

1.1. Composition 1, wherein the inorganic salt of peroxymonosulfate is an alkaline earth metal salt or a mixture thereof;

1.2. Composition 1 or 1.1, wherein the inorganic salt of peroxymonosulfate is sodium peroxymonosulfate, potassium peroxymonosulfate, or ammonium peroxymonosulfate;

1.3. Any of the preceding compositions, wherein the inorganic salt of peroxymonosulfate is potassium peroxymonosulfate;

1.4. Any of the preceding compositions, wherein the drying agent comprises calcium lactate, calcium lactophosphate, double salts of calcium lactate, phosphates, pyrophosphates, polyphosphates, orthophosphates, metaphosphates, silica, alumina, bicarbonates, polymetaphosphates, aluminum silicate, zirconium silicates, bentonite, and combinations thereof;

1.5. Any of the preceding compositions, wherein the drying agent comprises a pyrophosphate, alumina, sodium bicarbonate, or combinations thereof;

1.6. Any of the preceding compositions, wherein the drying agent comprises an alkali metal salt of pyrophosphate, e.g., tetrasodium pyrophosphate or tetrapotassium pyrophosphate;

1.7. Any of the preceding compositions, wherein the composition is in the form of a tablet, powder or granule and is packaged in a moisture free environment;

1.8. Any of the preceding compositions, wherein the composition is packaged in a single-use container comprising a tin can, tube, or sachet;

1.9. Any of the preceding compositions, wherein the composition contains no water or water in an amount of less than 4%, or less than 3%, or less than 2%, or less than 1%, or less than 0.5%, or about 0.0001% to about 4%, or about 0.0001% to about 0.5% or about 0.0001% to about 0.1%, or about 0.001% to 4%, by weight;

1.10. Any of the preceding compositions, wherein the inorganic salt of peroxymonosulfate is present in an amount of about 0.5% to about 50%, about 0.75% to about 40%, about 0.75% to about 37%, or about 7.5% to about 15% by weight of the total composition;

1.11. Any of the preceding compositions, wherein the drying agent is present in an amount of about 0.1% to about 60%, about 1% to about 30%, about 1% to about 10%, or about 1% to about 5%, or about 2%, or about 3%, or about 4% or about 5%, by weight of the total composition;

1.12. Any of the preceding compositions, wherein the particulated inorganic salt of peroxymonosulfate and the particulated drying agent have particle sizes from about 0.1 to about 1 mm, about 1 to about 500 microns, about 1 to about 250 microns, about 1 to about 150 microns, about 5 to about 100 microns, about 6 to about 35 microns, about 6 to about 13 microns in average diameter of individual particles;

1.13. Any of the preceding compositions, wherein the inorganic salt of peroxymonosulfate is potassium peroxymonosulfate in an amount of about 0.5% to about 50%, or about 0.75% to about 40%, or about 0.75% to about 37%, or about 7.5% to about 15%, by weight of the total composition;

1.14. Any of the preceding compositions, comprising a disintegrating agent is selected from natural starches, such as maize starch, potato starch; directly compressible starches such as starch 1500; modified starches such as carboxymethyl starches and sodium starch glycolate; starch derivatives such as amylose; cross-linked polyvinylpyrrolidones, such as crospovidones; modified celluloses such as cross-linked sodium carboxymethylcelluloses; alginic acid; sodium alginate; microcrystalline cellulose; methacrylic acid-divinylbenzene copolymer salts; light silicic anhydride; calcium silicate; magnesium metasilicate aluminate; carboxymethyl cellulose; and mixtures thereof;

1.15. Any of the preceding compositions, comprising a binder wherein the binder is selected from starches, natural gums, (e.g., xanthan gum), cellulose gums, microcrystalline cellulose, maltodextrins, methylcellulose, cellulose ethers, sodium carboxymethylcellulose, ethylcellulose, gelatin, polyethylene glycol, polyvinylpyrrolidone, pectins, alginates, polyacrylamides, polyvinyloxazolidone, polyvinyl alcohols and mixtures thereof;

1.16. The immediately preceding composition, wherein the binder is present in the composition in an amount of from 10% by weight to about 60% by weight, or from about 15% by weight to about 50% by weight, or from about 25% by weight to about 40% by weight;

1.17. Any of the preceding compositions, further comprising a buffering agent selected from an anhydrous carbonate such as sodium carbonate, a sesquicarbonate, a bicarbonate such as sodium bicarbonate, a silicate, a bisulfate, a citrate, a phosphate such as monopotassium phosphate and dipotassium phosphate, or a combination thereof in an amount of about 5.0% to about 35%, or about 10% to about 30%, or about 15% to about 25%, by weight of the total composition;

1.18. Any of the preceding compositions, wherein the composition is effervescent and contains an effervescent acid and an effervescent base;

1.19. The immediately preceding composition, wherein the effervescent acid is citric acid, ascorbic acid, malic acid, adipic acid, tartaric acid, fumaric acid, succinic acid, sodium acid pyrophosophate, lactic acid, hexamic acid, citraconic anhydride, glucono-D-lactone, succinic anhydride, potassium bitartrate, acid citrate salts, sodium dihydrogen phosphate, disodium dihydrogen phosphate, sodium acid sulfite, and combinations thereof, and is present in the composition in an amount of from 10% by weight to about 60% by weight, from about 15% by weight to about 50% by weight, or even from about 25% by weight to about 40% by weight;

1.20. The immediately preceding two compositions, wherein the effervescent base is sodium bicarbonate, sodium carbonate, sodium sesquicarbonate, potassium carbonate, potassium bicarbonate, calcium carbonate, magnesium carbonate, magnesium oxide, sodium glycine carbonate, L-lysine carbonate, arginine carbonate, zinc carbonate, zinc oxide and mixtures thereof, and is present in the composition in an amount of from 10% by weight to about 60% by weight, or from about 15% by weight to about 50% by weight, or from about 25% by weight to about 40% by weight;

1.21. Any of the preceding compositions, comprising a lubricant in an amount from about 1% by weight to about 15% by weight, or from about 1% by weight to about 12% by weight, or from about 2% by weight to about 10% by weight, or from about 3% by weight to about 8% by weight;

1.22. Any of the preceding compositions, containing an additional whitening agent;

1.23. Any of the preceding compositions, additionally comprising one or more flavor agents, one or more fillers, one or more surfactants, one or more color agents, or any combination of two or more thereof.

1.24. Any of the preceding compositions which is a toothpowder.

1.25. Any of the preceding compositions wherein the drying agent is not abrasive silica.

EXAMPLES

Exemplary embodiments of the present disclosure will be illustrated by reference to the following examples, which are included to exemplify, but not to limit the scope of the present invention.

In the examples and elsewhere in the description of the invention, chemical symbols and terminology have their usual and customary meanings. Temperatures are in degrees Celsius unless otherwise indicated. The amounts of the components are in weight percent based on the standard described; if no other standard is described then the total weight of the composition is to be inferred. Various names of chemical components include those listed in the CTFA International Cosmetic Ingredient Dictionary (Cosmetics, Toiletry and Fragrance Association, Inc., $7^{th}$ ed. 1997).

Example 1: One-Month Potassium Peroxymonosulfate Stability Study

Potassium peroxymonosulfate is added to four powdered samples and stored for one month. The samples are each stored at room temperature in an environment of 60% relative humidity. After 15 days and after 1 month, the relative weight percentage of active oxygen in the powdered samples is measured to determine the effectiveness of various drying agents. Sample 1 is formulated to include 3% tetrapotassium pyrophosphate (TKPP). Sample 2 is formulated to include 5% alumina. Sample 3 is formulated to include 3% sodium bicarbonate. A control sample is formulated having no drying agent. Each sample has an initial theoretical value of active oxygen of 0.478 wt %, based on the total weight of the composition.

TABLE 1

One-Month Stability Observations at Room Temperature

| | Control Sample 1 (no drying agent), wt % observed active oxygen | Sample 1 (3% TKPP), wt % observed active oxygen | Sample 2 (5% Alumina), wt % observed active oxygen | Sample 3 (3% Sodium Bicarbonate), wt % observed active oxygen |
|---|---|---|---|---|
| Initial | 0.44 | 0.43 | 0.44 | 0.44 |
| 15 days | 0.43 | 0.43 | 0.36 | 0.32 |
| 1 month | 0.42 | 0.45 | 0.33 | 0.31 |

As shown in Table 1 above, the sample including 3% tetrapotassium pyrophosphate (TKPP) shows surprisingly superior oxidizing agent stability in comparison to Sample 2 and Sample 3. The potassium peroxymonosulfate in Sample 1 shows 36% less degradation than Sample 2 and 39% less degradation than Sample 3 over the course of one month.

A similar study is conducted on samples stored at 40° C. in an environment of 75% relative humidity. These conditions are selected to mimic accelerated aging conditions or those conditions at which it is particularly difficult to maintain stability of potassium peroxymonosulfate. Each sample has an initial theoretical value of active oxygen of 0.478 wt %, based on the total weight of the composition.

TABLE 2

One-Month Stability Observations at 40° C.

| | Control Sample 1 (no drying agent), wt % observed active oxygen | Sample 1 (3% TKPP), wt % observed active oxygen | Sample 2 (5% Alumina), wt % observed active oxygen | Sample 3 (3% Sodium Bicarbonate), wt % observed active oxygen |
|---|---|---|---|---|
| Initial | 0.44 | 0.43 | 0.44 | 0.44 |
| 15 days | 0.4 | 0.4 | 0.29 | 0.28 |
| 1 month | 0.36 | 0.37 | 0.26 | 0.25 |

As shown in Table 2 above, the sample including 3% tetrapotassium pyrophosphate (TKPP) again shows surprisingly superior stability in comparison to Sample 2 and Sample 3. The potassium peroxymonosulfate in Sample 1 shows 42% less degradation than Sample 2 and 48% less degradation than Sample 3 over the course of one month.

Example 2: Three-Month Potassium Peroxymonosulfate Stability Study in Various Packaging Potassium peroxymonosulfate is added to four additional powdered samples and stored for three months. The samples are each stored at room temperature in an environment of 60% relative humidity. After 15 days, 1 month, 2 months, and 3 months, relative weight percentages of active oxygen in the powdered samples are measured to determine the effectiveness of tetrapotassium pyrophosphate (TKPP) as a drying agent. Sample 4 is formulated to include 3% tetrapotassium pyrophosphate (TKPP) and is stored in a tin can. Sample 5 is formulated to include 3% tetrapotassium pyrophosphate (TKPP) and is stored in a sachet. Control sample 2 is formulated having no drying agent and is stored in a tin can. Control sample 3 is formulated having no drying agent and is stored in a sachet. Each sample has an initial theoretical value of active oxygen of 0.478 wt %, based on the total weight of the composition.

TABLE 3

Three-Month Stability Observations at Room Temperature in Various Packaging

| | Control Sample 2 (without drying agent in tin can), wt % observed active oxygen | Control Sample 3 (without drying agent in sachet), wt % observed active oxygen | Sample 4 (3% TKPP in tin can), wt % observed active oxygen | Sample 5 (3% TKPP in sachet), wt % observed active oxygen |
|---|---|---|---|---|
| Initial | 0.41 | 0.44 | 0.44 | 0.43 |
| 15 days | 0.34 | 0.43 | 0.43 | 0.43 |
| 1 month | 0.35 | 0.42 | 0.38 | 0.45 |
| 2 months | 0.25 | 0.46 | 0.36 | 0.44 |
| 3 months | 0.23 | 0.37 | 0.32 | 0.37 |

As shown in Table 3 above, Sample 4 containing 3% tetrapotassium pyrophosphate (TKPP) stored in the tin can shows superior results in comparison to Control Samples 2, but Sample 5 containing 3% tetrapotassium pyrophosphate (TKPP) stored in the sachet shows similar results to Control Sample 3.

A similar study is conducted on samples stored at 40° C. in an environment of 75% relative humidity. These conditions are selected to mimic accelerated aging conditions or those conditions at which it is particularly difficult to maintain stability of potassium peroxymonosulfate. Each sample has an initial theoretical value of active oxygen of 0.478 wt %, based on the total weight of the composition.

TABLE 4

Three-Month Stability Observations at 40° C. in Various Packaging

| | Control Sample 2 (without drying agent in tin can), wt % observed active oxygen | Control Sample 3 (without drying agent in sachet), wt % observed active oxygen | Sample 4 (3% TKPP in tin can), wt % observed active oxygen | Sample 5 (3% TKPP in sachet), wt % observed active oxygen |
|---|---|---|---|---|
| Initial | 0.41 | 0.44 | 0.44 | 0.43 |
| 15 days | 0.28 | 0.4 | 0.29 | 0.4 |
| 1 month | 0.16 | 0.36 | 0 | 0.37 |
| 2 months | 0.03 | 0.34 | 0.01 | 0.47 |
| 3 months | 0 | 0.3 | 0.01 | 0.42 |

As shown in Table 4 above, Sample 5 including 3% tetrapotassium pyrophosphate (TKPP) stored in the sachet shows surprisingly superior results in comparison to Control Samples 2 and 3. The samples stored in the tin can show effectively no remaining active oxygen after a period of 3 months, regardless of whether tetrapotassium pyrophosphate (TKPP) is included in the composition. However, the vast majority of potassium peroxymonosulfate remains intact in Sample 5, which shows 40% less degradation than Control Sample 3, containing no tetrapotassium pyrophosphate (TKPP) and stored in a sachet.

Example 3: Potassium Peroxymonosulfate Stability after Direct Contact to Atmosphere The effect of short-term direct exposure to atmosphere on a powdered composition of potassium peroxymonosulfate is tested. In the test, a composition comprising potassium peroxymonosulfate and tetrapotassium pyrophosphate (TKPP) is prepared and loaded into a sachet as in Example 2. The sachet is opened at room temperature and left undisturbed for a period of eight hours to mimic partial use by a consumer. The sample has an initial theoretical value of active oxygen of 0.478 wt %, based on the total weight of the composition. The initial measurement of observed active oxygen in the sample is about 0.43 wt %. After a period of eight hours, it is observed that the composition still has about 0.41 wt % active oxygen, based on the total weight of the composition. Thus, it can be concluded that tetrapotassium pyrophosphate (TKPP) can permit potassium peroxymonosulfate to withstand short periods of direct exposure to atmosphere without substantial degradation.

Example 4: Three-Month Potassium Peroxymonosulfate Comparative Stability Study

Potassium peroxymonosulfate mixed with specific drying agents is stored as a powder in sachets at either room temperature at 60% relative humidity, or at 40° C. at 75% relative humidity, as described in the preceding examples. After 3 months, relative weight percentages of active oxygen in the powdered samples are measured to determine the effectiveness of the drying agent.

TABLE 5

Three-Month Comparative Stability Observations at RT and 40° C.

|  | Control Sample 4 (no dryin gagent) | Sample 6 (5% TKPP) | Sample 7 (10% TKPP) | Sample 8 (1% TKPP) | Control Sample 5 (3% sodium sulfate) | Control Sample 6 (3% Abrasive Silica) |
| --- | --- | --- | --- | --- | --- | --- |
| Initial, RT | 0.39 | 0.44 | 0.44 | 0.44 | 0.44 | 0.40 |
| 1 month, RT | 0.23 | 0.43 | 0.43 | 0.38 | 0.29 | 0.29 |
| Initial, 40° C. | 0.39 | 0.44 | 0.44 | 0.44 | 0.44 | 0.40 |
| 1 month, 40° C. | 0.20 | 0.39 | 0.38 | 0.27 | 0.13 | 0.19 |

As shown in Table 5, both 5% and 10% TKPP are approximately equally effective in maintaining the stability of the oxidizing agent, while 1% TKPP not as effective, and both sodium sulfate and abrasive silica (both well-known desiccants) are not effective in maintaining stability. Indeed, under the high temperature accelerated aging conditions, both sodium sulfate and abrasive silica result in less stability than a control which is free of any drying agent.

The invention has been described above with reference to illustrative Examples, but it is to be understood that the invention is not limited to the disclosed embodiments. Alterations and modifications that would occur to one of skill in the art upon reading the specification are also within the scope of the invention, which is defined in the appended claims.

What is claimed is:

1. A tooth whitening storage-stable solid composition comprising:
    a tooth whitening effective amount of potassium peroxymonosulfate; wherein the potassium peroxymonosulfate is present in an amount of about 7.5% to about 15% by weight of the total composition;
    one or more flavor agents;
    one or more sweeteners; and
    a particulated drying agent comprising tetrapotassium pyrophosphate salt present in an amount of about 3% to about 5% by weight of the total composition;
    wherein the potassium peroxymonosulfate agent is the only peroxide whitening agent in the composition, wherein the composition is an oral care formulation formulated as a toothpowder.

2. The composition of claim 1, wherein the drying agent further comprises calcium lactate, calcium lactophosphate, double salts of calcium lactate, phosphates, polyphosphates, orthophosphates, metaphosphates, silica, alumina, bicarbonates, polymetaphosphates, aluminum silicate, zirconium silicates, bentonite, and combinations thereof.

3. The composition of claim 1, wherein the drying agent further comprises tetrasodium pyrophosphate.

4. The composition of claim 1, wherein the composition is packaged in a single-use container comprising a tin can, tube, or sachet.

5. The composition of claim 1, wherein the composition contains water in an amount of less than 4%, or less than 1%, or less than 0.5% by weight of the composition.

6. The composition of claim 1, wherein the tetrapotassium pyrophosphate is present in an amount of about 3% by weight of the total composition.

7. The composition of claim 1, wherein the potassium peroxymonosulfate and the tetrapotassium pyrophosphate have particle sizes from about 0.1 to about 1 mm in average diameter of individual particles.

8. The composition of claim 1, further comprising one or more fillers, one or more surfactants, one or more color agents, or any combination of two or more thereof.

9. A method for whitening teeth comprising the steps of: mixing the storage-stable solid composition of claim 1 into water, a mouthrinse base, or a paste base until the composition dissolves; and applying the composition to the surfaces of the oral cavity and the teeth.

10. The composition of claim 1, wherein the composition contains no water.

11. The composition of claim 1, wherein the composition consists of the potassium peroxymonosulfate, the tetrapotassium pyrophosphate, and one or more other agents selected from additional drying agents, disintegrating agents, binders, lubricants, fillers, surfactants, and/or color agents.

12. The method according to claim 9, wherein the composition is mixed with water or a mouthrinse base to form a mouthrinse.

13. The method according to claim 9, wherein the composition is mixed with water or a paste base to form a toothpaste.

14. The method according to claim 9, wherein the composition consists of the potassium peroxymonosulfate, the tetrapotassium pyrophosphate, and one or more other agents selected from additional drying agents, disintegrating agents, binders, buffering agents, lubricants, fillers, surfactants, and/or color agents.

* * * * *